US007449341B2

(12) United States Patent
Ginot et al.

(10) Patent No.: US 7,449,341 B2
(45) Date of Patent: Nov. 11, 2008

(54) METHOD AND DEVICE FOR ISOLATION AND/OR DETERMINATION OF AN ANALYTE

(75) Inventors: Frederic Ginot, Voreppe (FR);
Jean-Luc Achard, Grenoble (FR);
Laurent Drazek, Orleans (FR); Pascale Pham, Crolle (FR)

(73) Assignees: Biomerieux, Marcy l'Etoile (FR);
Commissariat a l'Energie Atomique, Paris (FR)

( * ) Notice: Subject to any disclaimer, the term of this patent is extended or adjusted under 35 U.S.C. 154(b) by 947 days.

(21) Appl. No.: 10/488,208

(22) PCT Filed: Sep. 12, 2002

(86) PCT No.: PCT/FR02/03113

§ 371 (c)(1),
(2), (4) Date: Apr. 1, 2004

(87) PCT Pub. No.: WO03/022436

PCT Pub. Date: Mar. 20, 2003

(65) Prior Publication Data

US 2005/0064603 A1 Mar. 24, 2005

(30) Foreign Application Priority Data

Sep. 12, 2001 (FR) .................................. 01 11883

(51) Int. Cl.
*G01N 1/44* (2006.01)
(52) U.S. Cl. ...................................... 436/176; 436/174
(58) Field of Classification Search ............... 422/186.2
See application file for complete search history.

(56) References Cited

U.S. PATENT DOCUMENTS 3,807,353 A * 4/1974 Kobernick ................... 118/702
4,672,040 A * 6/1987 Josephson ................... 436/526
5,135,048 A * 8/1992 Behrle et al. ................. 165/96

OTHER PUBLICATIONS

Hanghui Liu, Purnendu K. Dasgupta, Analytical Chemistry in a Drop. Solvent Extraction in a Microdrop☐☐Analytical Chemistry, vol. 68, No. 11, Jun. 1, 1996.*
Hanghui Liu, Purnendu K. Dasgupta, Analytical Chemistry in a Drop.☐☐Trends in Analytical Chemistry, vol. 15, No. 9, 1996.*

* cited by examiner

*Primary Examiner*—Jill Warden
*Assistant Examiner*—Dwan A Gerido
(74) *Attorney, Agent, or Firm*—Oliff & Berridge, PLC

(57) ABSTRACT

The invention concerns a method for isolating an analyte from an initial sample containing same, on a reactive surface in contact with all or part of the initial sample, characterized in that it comprises the following steps which consist in: 1) forming and/or maintaining a reaction volume entity, comprising an internal liquid medium, corresponding to all or part of the initial sample, the entity including an interface with an external medium, having with the latter a surface tension; 2) applying a temperature difference between at least two thermal points located: a) proximate to and/or b) on the surface and/or c) within said entity, said thermal points being respectively different, in terms of temperature and positioning; 3) fixing the analyte on the reactive surface, positioned on the path of forces convection generated by the temperature difference.

14 Claims, 4 Drawing Sheets

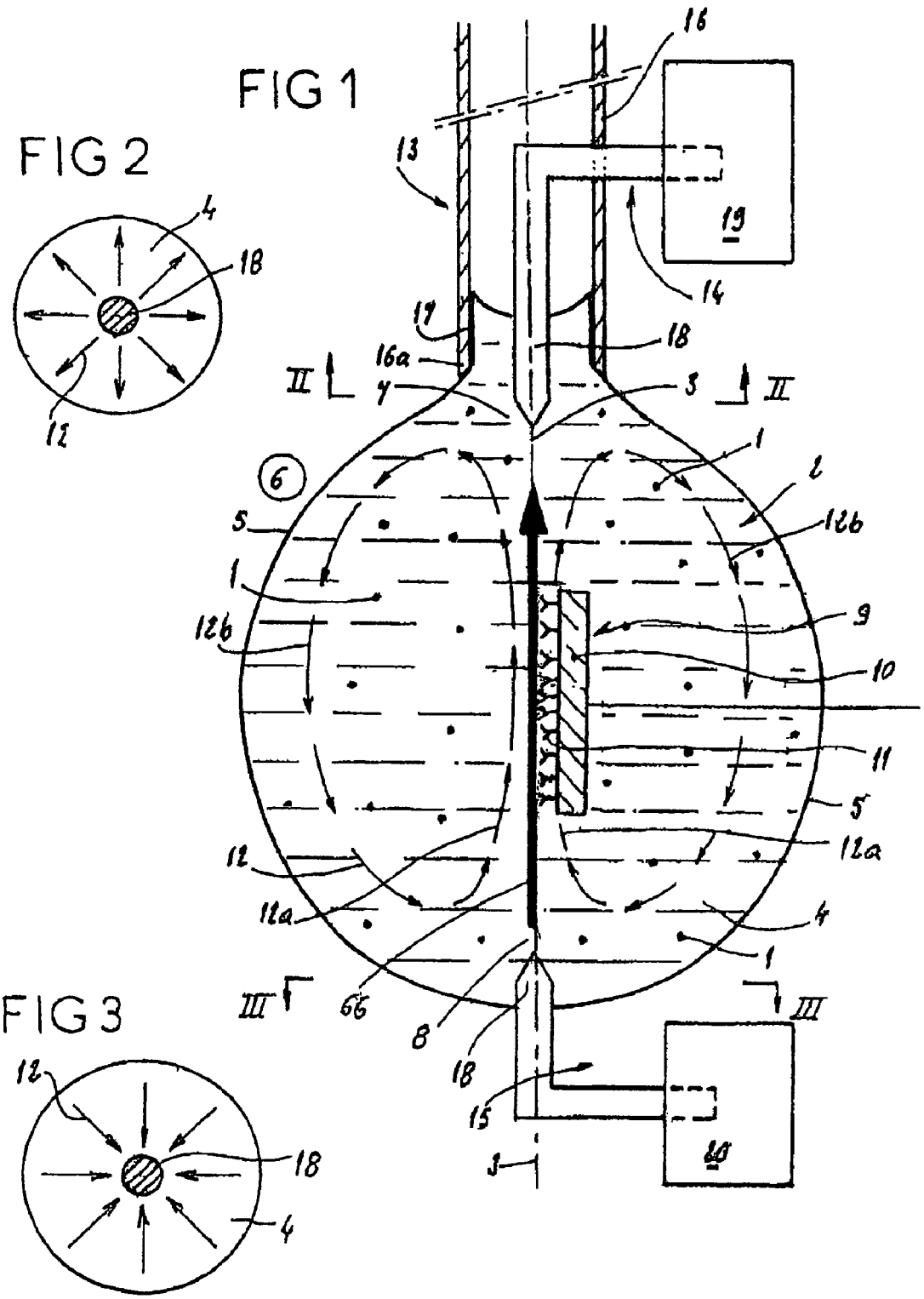

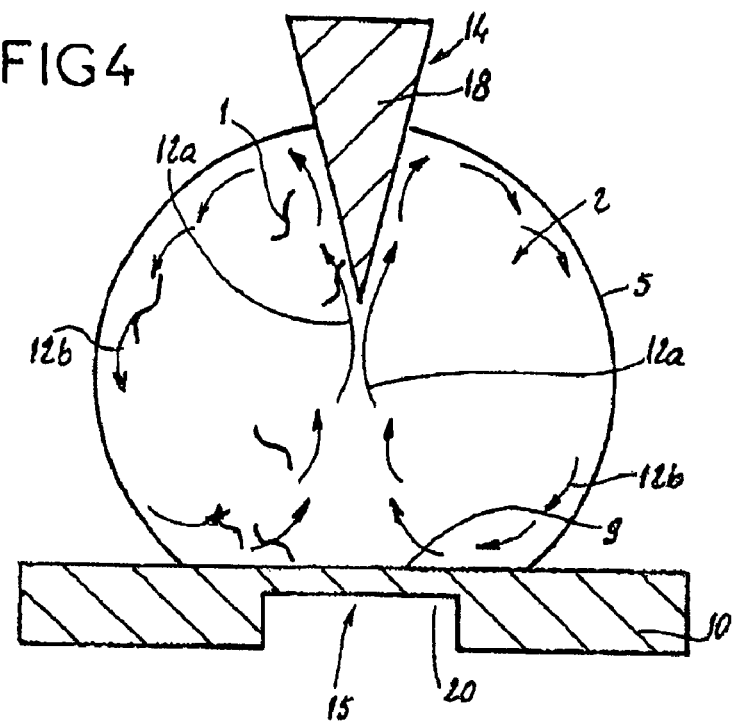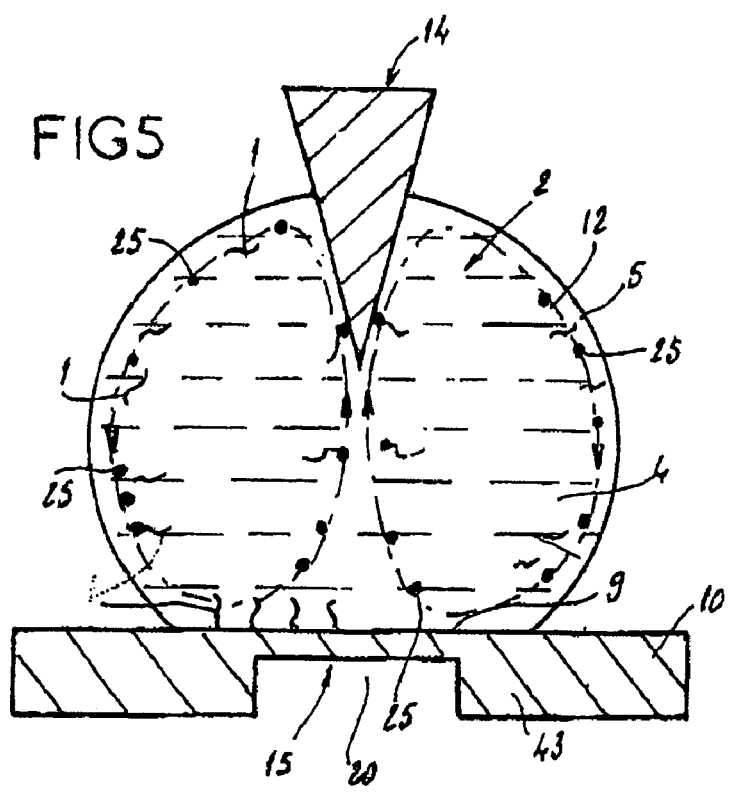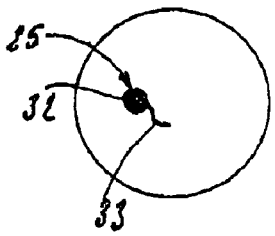

METHOD AND DEVICE FOR ISOLATION AND/OR DETERMINATION OF AN ANALYTE

Figure 7:
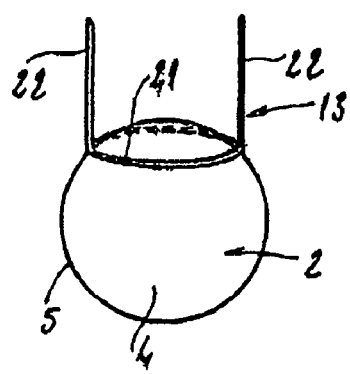

The present invention relates in general to the isolation of an analyte.

The terms "isolate" or "isolation" generally mean any technique for separating an analyte, or alternatively for enriching or concentrating said analyte in any liquid containing it, or any solid support in contact with this liquid. It may also mean, however, possibly in conjunction with the previous definition, any technique for determining the analyte in the sense of detecting and/or quantifying it, from the liquid medium containing it.

"Analyte" means any entity, particularly a chemical, biochemical or biological entity, to be isolated. Among the analytes considered below in the present invention, mention will be made of cells, organelles, viruses and bacteria, antibodies, antibody fragments, antigens, haptens, lectins, sugars, nucleic acids, proteins, in particular A or G, hormones, hormone receptors, biotin, avidin, streptavidin, and in general any natural or synthetic molecules or macromolecules, or analogs, to be determined, that is to say detected and/or quantified.

More particularly, the present invention will be introduced and discussed with reference to biological analyses, in particular molecular analyses, for which the initial liquid sample comprises or contains an analyte of the biological macromolecule type, such as a protein or nucleic acid.

Various heterogeneous-type biological assay formats, such as those referred to as ELISA, include a so-called incubation step during which an intermediate liquid medium, in which the analyte obtained from the initial sample is distributed, is brought in contact with a reactive surface, that is to say a surface obtained from a substrate and a specific analyte-binding reagent distributed and fixed on said surface.

The performance of such a step, the purpose of which is to capture the analyte, determines that of the analysis method being employed, in terms of specificity, sensitivity, precision or speed.

This performance in turn depends on a certain number of factors which ought to be examined in order to clearly understand the limits of the analysis methods currently employed in the field of molecular biology (for example nucleic acid analysis) and immunoassays.

One factor relates to the actual exposure of the active surface to any analyte distributed in the liquid medium. In practice, molecular diffusion (by thermal agitation) on its own is insufficient to bring the analyte molecules to the reactive surface, since they are separated from said surface by a distance of more than a few hundreds of microns. When simple diffusion is used, only a limited quantity of the analyte will consequently reach the reactive surface.

Various solutions have been proposed in order to overcome the limits of molecular diffusion in general:

a) it has been proposed to agitate the liquid medium in contact with the reactive surface; such a solution no longer works when the volume of the liquid medium is relatively small or the well is too deep, as is the case with the wells of a microtitration plate having 384 or more wells, the elementary volume of which may not be more than 200 µl per well, b) it has also been proposed to create a flow of the liquid medium, in general a laminar flow, in contact with the reactive surface. This solution makes it necessary to use a mechanical pump and to set relatively large volumes in motion, which reduces the rate of specific binding between the reactive surface and the analyte, c) it has also been proposed to reduce the quantity of the liquid medium, while employing an intermediate reagent in the divided state, for example magnetic particles comprising a magnetic support and an analyte capture agent bound to said support. This intermediate reagent makes it possible to capture the analyte, and can subsequently be confined using a magnetic field. This confinement makes it possible to remove the excess liquid medium without taking the analyte with it. By breaking down the binding between the intermediate reagent and the analyte, for example using heat, the latter is then released into a much smaller volume of the liquid medium.

This solution has the drawback of requiring an extra reagent and several additional operating steps.

d) it has also been proposed to divide and distribute the reactive surface inside the liquid medium, using a magnetic support which is divided in the form of particles and is functionalized with the specific analyte-binding reagent. These particles have a size of between 50 nm and several microns. Once they have reacted with the analyte, these particles can subsequently be separated by magnetic confinement as before.

This solution has the advantage of increasing the requisite analyte capture area since the specific binding reagent is present everywhere, or almost. The problem, however, arises while carrying out the test, when the analyte is being revealed using a detection reagent. This detection reagent will also become fixed on the reactive area, at a small but nonzero level, regardless of whether or not the analyte is present. A quantity, proportional to the reactive area, of detection analyte not specifically bound to the analyte will generate background noise which reduces the sensitivity of the incubation step and therefore that of the analysis method.

Another factor relates precisely to the size of the nonreactive (because they are not functionalized with the specific binding reagent) surfaces brought in contact with the analyte. These surfaces will in general retain some of the analyte, for example by absorption, which of course reduces the quantity of analyte actually captured by the reactive surface proper, and therefore limits the sensitivity of the incubation step and hence of the analysis method.

It is therefore beneficial to limit the size of the surfaces in contact with the liquid medium, other than the reactive surface proper.

The present invention relates to a method for accelerating the kinetics when bringing the analyte in contact on the reactive surface.

The solution according to the invention breaks with the traditional methods of analysis, in particular biological analysis, by providing a method, in particular for incubation, consisting at least in:

1) forming and/or maintaining for the duration of said step a reaction volume unit having a shape which is symmetrical about a reference axis, consisting only of a so-called internal liquid medium in which the analyte obtained from some or all of the initial liquid sample is distributed, said reaction unit having an interface with an optionally confined external medium which is different to the internal medium, and having a surface tension with respect to it, said interface having a closed developed surface about said reference axis, 2) generating a thermal gradient through the reaction unit along the reference axis, so as to define a hot region and a cold region therein and to induce a variation in the surface tension of the interface, parallel to the reference axis, and to set the internal medium in motion along a closed path of forced microconvection, comprising an axial forward circulation from the cold region to the hot region and a peripheral return circulation from the hot region to the cold region, 3) placing the reactive surface in contact with the internal medium of the reaction unit in the forced microconvection path of said internal medium.

By virtue of the invention, there is virtually no dead volume inside the liquid medium, and almost all of the liquid constituting the internal medium will be brought in contact with the active surface.

The solution according to the invention therefore makes it possible to directly increase the sensitivity of the method for determining the analyte, and therefore to further improve the efficiency of techniques such as amplification involving an analyte of the nucleic acid type.

The specific binding reagent is preferably a ligand.

"Ligand" means an element capable of forming a complex with the analyte by physical binding.

Examples of ligands which may be mentioned are antibodies, antibody fragments, antigens, haptens, lectins, sugars, nucleic acids, proteins, in particular A or G, hormones, hormone receptors, biotin, avidin, streptavidin, and in general natural or synthetic ligands and modified ligand analogs, which may enter into competition with ligands.

Any ligand as defined above is immobilized on a support by some means such as adsorption, covalence, chelation, molecular recognition, and is capable of retaining the analyte, on its own or conjugated with another ligand.

"Support" means any type of polymeric, inorganic or metal support. Examples of polymeric supports which may be mentioned are plastic supports based on polystyrene, poly(meth)acrylates, polybutadienes, polypropylene or the like, individually or in the form of copolymers. Examples of inorganic supports which may be mentioned are silicon oxide, silicon, mica, glass, quartz, titanium oxide, vanadium oxide. Examples of metal supports which may be mentioned are gold, silver.

The immobilization of the ligands on the support may be carried out either by simple adsorption onto the native or modified support, or by means of a chemical-functionalizing or physical reaction for modifying the surface of the support, and hence for making it possible to fix the receptor by covalent bonds, or other traditional means well known to the person skilled in the art.

In the following description, "particle" means any particle of a polymeric, inorganic or metal support onto which a ligand can be grafted. In particular, particles which can be separated by the action of an external physical means, for example magnetically or electrically, or under the effect of gravity or by centrifuging, are considered as falling within the scope of the present invention. The previous description includes particles of small size, especially superparamagnetic particles, the sedimentation rate of which under the effect of gravity is less than thermal agitation but which can form aggregates, by any method of joining them together or assembling them on particles of larger size, which are separable by any physical means.

Examples of polymeric particles which may be mentioned are particles obtained by emulsion polymerization, such as latexes, or particles of larger size, either magnetic or nonmagnetic.

Examples of metal particles which may be mentioned are colloidal gold, ferro-, ferri-, para- or superparamagnetic particles, optionally covered with natural or synthetic polymers, the composition of which comprises iron or other metals such as cobalt, nickel, individually or in the form of alloys, either magnetic or nonmagnetic.

Examples of inorganic particles which may be mentioned are particles based on silica or silicon, either magnetic or nonmagnetic.

"Determination" means any method for demonstrating the presence of the analyte bound to the reactive surface, and/or for quantifying it.

Examples of determination methods which may be mentioned are any traditional methods, for example with the aid of a label, particularly using fluorescence, and in general all equivalent techniques not mentioned here, for example calorimetric, enzymatic or chronogenic methods.

Figure 12:
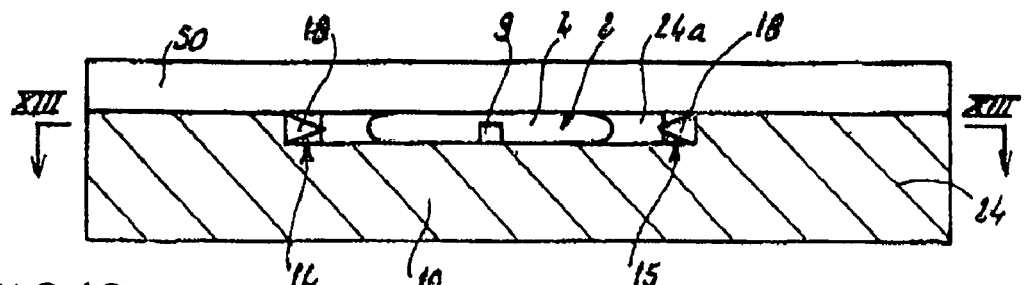
Figure 13:
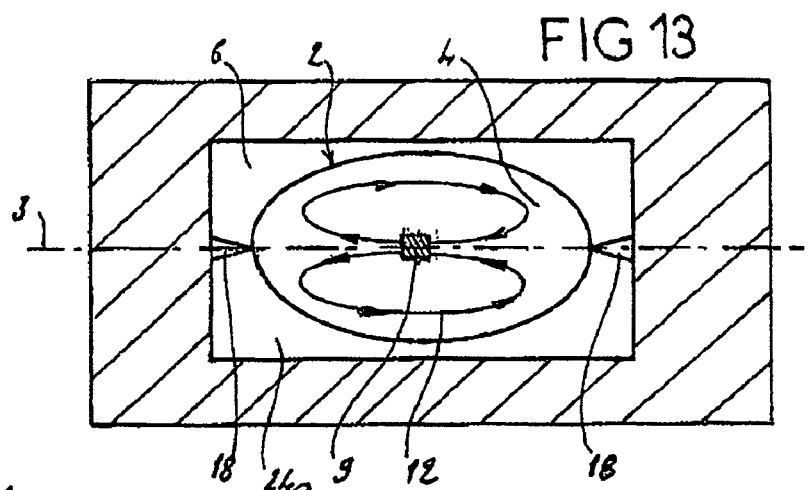
Figure 14:
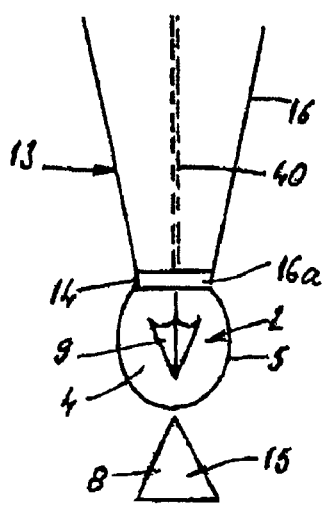
Figure 15:
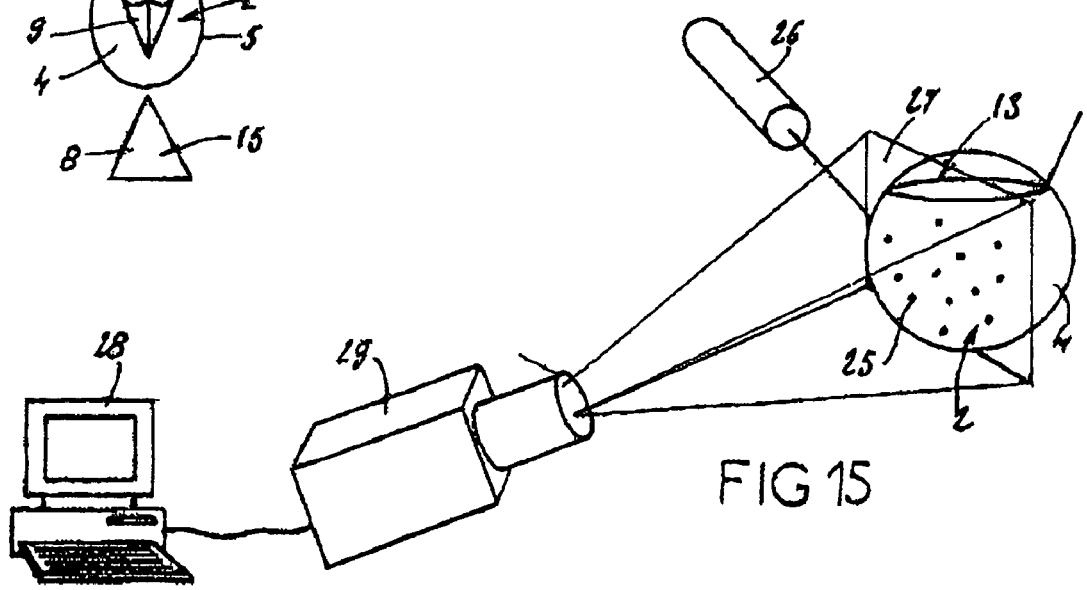

The present invention will now be described with reference to the appended drawings, in which:

FIG. 1 schematically represents a device according to the present invention on an enlarged scale; FIGS. 2 and 3 represent a sectional view of the device according to FIG. 1, respectively on sections II-II and III-III; it is on the basis of these FIGS. 1 to 3 that the method according to the invention and its principles will be explained, FIGS. 2, 4 on the one hand, and 5 and 6 on the other hand, respectively represent two other embodiments of a device according to the invention, also schematically; the detail represented, or schematized, by FIG. 6 shows a particle or microparticle as will be considered here in the present invention, combined with an analyte capture agent, FIGS. 7 to 11 respectively represent other alternative embodiments of a device according to the invention, schematically and in partial views, FIG. 12 represents another alternative embodiment of a device according to the invention, also schematically, from the side and partially in section;

FIG. 13 is a view in section on XIII-XIII of the device shown in FIG. 12,

FIG. 14 schematically represents another alternative embodiment of the present invention, FIG. 15 schematically represents an experimental setup, which made it possible to demonstrate the relevance of the method according to the invention, as employed with any one of the microanalysis devices according to FIGS. 1 to 14.

Referring to FIG. 1, a device according to the invention comprises:

a)—Means (13) for forming and/or maintaining a reaction volume unit (2), for example a drop, having a shape which is symmetrical about at least one reference axis (3); this drop consists only of a liquid medium, referred to below as the internal medium (4), in which an analyte is distributed (in solution and/or suspension); this reaction unit (2) has an interface (5) of convex overall profile with an external medium 6, which is different to the internal medium, so that the internal and external media (4 and 6, respectively) have a surface tension between them; and the interface (5) has a closed developed surface about the reference axis (3), b)—Means (14, 15) for applying a temperature difference, which are arranged with respect to the means (13) for forming and/or maintaining the reaction unit (2) so as to align a thermal gradient (66) with the reference axis (3) through the reaction unit (2), and so as to define a so-called hot region (7) and a so-called cold region (8) on either side of the reference axis (3) therein; this thermal gradient induces a variation in the surface tension of the interface (5), parallel to the reference axis (3), which sets the internal medium (4) in motion along a closed path (12) of forced microconvection, comprising an axial forward circulation (12a) from the cold region (8) to the hot region (7) and a peripheral return circulation (12b) from the hot region (7) to the cold region (8), c)—A reactive surface (9) obtained from a substrate (10) on which a reagent (11) for specific binding with the analyte (1) is fixed, the binding reagent being distributed and fixed on said substrate (by covalent chemical bonding and/or adsorption); the reactive surface (9) is arranged with respect to the means (13) for forming and/or maintaining the reaction unit (2) so as to be placed in contact with the internal medium (4) in the forced microconvection path (12) of the internal medium (4).

The means (13) for forming and/or maintaining the reaction unit (2) comprise a tube (16), for example a capillary tube, the open free end (16a) of which is designed to form and suspend the reaction unit (2), that is to say a drop of the internal medium (4). The inside of the tube (16) is lined with a layer (17) of a hydrophilic material, limited in length or in height to the free end (16a), and a layer of a hydrophobic material optionally lines the rest of the inner surface of said tube (16).

The means for generating the thermal gradient (66) comprise heating means (14) which exchange heat with the internal medium (4) of the reaction unit (2), on the same side as the hot region (7), and cooling means (15) which extract heat from the aforementioned internal medium (4), on the same side as the cold region (8).

By way of example, and without implying any limitation, the heating means (14) and/or the cooling means (15) comprise a metal element (18), the free end of which is pointed or beveled, arranged coaxially with the reference axis (3) and immersed at its free end in the internal medium (4) of the reaction unit (2). The same metal element is thermally connected at the other end to a heat source (19), or to a cooling source (20) as applicable. Each of these sources may consist of a thermostatted liquid bath, or of a PELTIER-effect thermal module.

By way of example, the heating means (14) or the cooling means (15) consist of the external medium; alternatively, the heating means (14) and/or the cooling means (15) consist of one or more metal elements (18).

Although this is not represented, the device according to the invention comprises an enclosure for confinement of the external medium (6), for example ambient air saturated with moisture.

The device described above makes it possible to carry out, or can be integrated in, any method for isolating the analyte (1) from an initial sample containing it. This device makes it possible to carry out a method comprising the following steps, irrespective of their chronological order.

a)—Forming and/or maintaining the reaction volume unit (2) having a shape which is symmetrical about at least one reference axis (3), this unit consisting only of a liquid medium, or internal medium (4), in which the analyte (1) obtained from some or all of the initial sample is distributed; as mentioned above, this reaction unit (2) has an interface (5) with the optionally confined external medium (6), this external medium being different to the internal medium (4) and therefore having a surface tension with respect to it; as shown by FIG. 1, the interface (5) has a closed developed surface of convex profile about said reference axis (3).

b)—By applying a temperature difference, generating a thermal gradient (66) through the reaction unit (2) along the reference axis (3), so as to define the hot region (7) and the cold region (8) therein; as mentioned above, it is this thermal gradient that induces a variation in the surface tension along the interface (5), parallel to the reference axis (3), and which sets the internal medium (4) in motion along a closed path (12) of forced microconvection, comprising both an axial forward circulation (12a) from the cold region (8) to the hot region (7) and a peripheral return circulation (12b) from the hot region (7) to the cold region (8)

c)—Optionally providing or obtaining the reactive surface (9), comprising the substrate (10) and the reagent (11) for specific binding with the analyte (1), this binding reagent being distributed and fixed on this surface.

d)—Placing the reactive surface (9) in the forced microconvection path (12) of the internal medium (4).

The reaction volume unit (2) preferably has a volume at most equal to 300 µl, and preferably lying between 0.1 and 100 µl, for example a few tens of µl. The volume of 5 µl is used because it corresponds to the volume of a drop.

The surface tension of the internal medium (4), with respect to the external medium (6), is at least equal to 10 N/m, and preferably lies between $10^{-2}$ and 1 N/m.

The internal liquid medium preferably comprises water, and is for example an aqueous solution in which the analyte (1) is suspended and/or dissolved. When the analyte is of the biological ligand type, such as an antibody or antigen, or a nucleotide sequence, for example, the internal liquid medium is a buffer comprising various ingredients or agents in addition to water, such as salts, organic compounds etc. In this case, the external medium (6) is preferably air laden with water vapor.

As shown by FIG. 1, the reference axis (3) is arranged vertically, and the thermal gradient (66) may correspondingly be arranged from the bottom upward.

This thermal gradient (66) is therefore generated by extracting heat from the internal medium (4) in the cold region (8) of the reaction unit (2), and supplying heat to it in the hot region (7) of the same reaction unit, for example using the means described above, although it should be understood that heat may be supplied to the hot region (7) or extracted from the cold region (8) by any other means; for instance, heat may be supplied by illuminating the hot region (7) with an infrared or laser beam.

As shown in FIG. 1, the thermal gradient (66) is generated by supplying the internal medium (4) with heat in the hot region (7) of the reaction unit (2), and the heat is supplied, for example, by conductive exchange with a heating element in the form of a metal rod (18) arranged at least partly inside the internal medium (4), on the same side as its hot end (7).

The reactive surface (9) is completely immersed in the internal medium (4), between the hot region (7) and the cold region (8), for example as close as possible to the reference axis (3).

The reactive surface (9) is preferably positioned as close as possible to the reference axis (3) because all of the forced microconvection paths (12) pass through there, as can be seen by studying FIGS. 1 to 3.

In order to maintain the integrity of the reaction unit (2), and in particular to provide it with a lifetime compatible with the time taken to carry out the method, the temperature in the hot region (7) of the reaction unit (2) is maintained at a value lower than the boiling temperature of the internal medium (4), and the temperature of the cold region (8) of the same unit is maintained at a value higher than the freezing temperature of said internal medium (4).

According to the invention, the rate of the forced microconvection of the internal medium (4) is controlled by variation of the thermal gradient (66), the nominal value of which is for example equal to 30° C.

Figure 8:
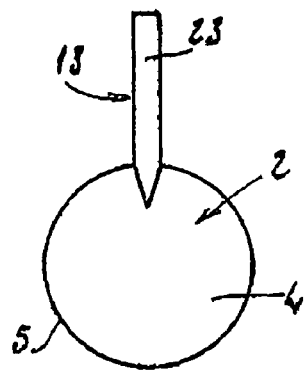
Figure 9:
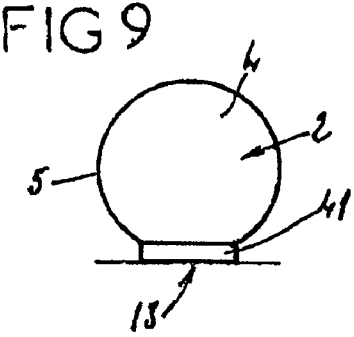
Figure 10:
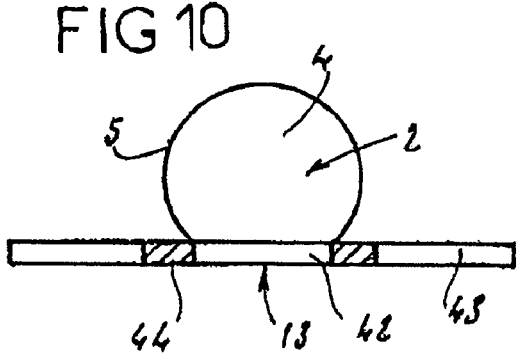

According to FIG. 4, the means (13) for forming and/or maintaining a reaction unit (2) comprise a means for placing it on a planar support, which may consist of a hydrophilic base (41), as shown in FIG. 9, or a hydrophilic region (42) of a support (43), which is circumscribed by a hydrophobic region (44), as shown in FIG. 8.

"Hydrophilic base" means a base whose upper surface is hydrophilic but whose side edges are not.

According to FIG. 5, the support limited and circumscribed at the outer surface of contact with the reaction unit (2) forms a substrate for the reagent (11) for specific binding with the analyte (1). The cooling means (15) are thermally connected to the support (43), for example by conduction, and consequently to the reactive surface (9) so that it becomes cooled.

According to FIG. 4, the schematically represented analyte (1) is a strand consisting of a nucleotide sequence of interest, for example belonging to a pathogenic agent such as a bacterium or virus.

As above, the heating means (14) may be thermally connected to the reactive surface (9), optionally by conduction.

In a manner which is known per se, as shown by FIGS. 5 and 6, the analyte (1) is bound to a particle (25), the latter comprising a support (32) and an agent (33) for capture of the analyte (1), which is bound to the support (32). The binding between the support (32) and the capture agent and/or between the capture agent and the analyte is labile at the temperature of the hot region (7) of the reaction unit (2), and effective at any temperature lying between that of the hot region (7) and that of the cold region (8) of the reaction unit (2). For the purpose of determining the analyte, these particles (25) are distributed and suspended in the internal medium of the reaction unit.

The metal element (18) belonging to the heating means (14) is magnetized, so as to generate a permanent or temporary magnetic field inside the internal medium (4) of the reaction unit (2), this magnetic field remaining spatially away from the reactive surface (9).

The effect of the forced microconvection along the path (12), in conjunction with the aforementioned properties of the intermediate reagent (25) in the form of particles, on the one hand, and the magnetic field incorporated in the heating means (14), on the other hand, is that:

the particles (25) capture the analyte in the upward axial circulation of the internal medium, then they are confined in contact with the heating means (14), for example the end of the rod (18), the labile particles (25) dissociate in contact with the heating means, and the dissociated parts are entrained together in the downward peripheral circulation of the internal medium until they come in contact with the reactive surface (9), the analyte (1) becomes specifically bound in contact with this surface (9), which is cooled, overall, since there is virtually no dead volume, that is to say volume unaffected by the forced microconvection, virtually all of the analyte (1) will be collected and entrained in contact with the reactive surface (9), and collected on it.

In this respect, reference will be made to FIGS. 5 and 6.

Any particle as defined above may be a magnetic particle that can be trapped by a magnetic source, such as a magnet. Such a magnetic source is located level with or belongs to the means generating the hot region (7).

According to FIG. 7, the means (13) for forming and/or maintaining the reaction unit (2) consist of a ring (21) suspended by two vertical and diametrically opposite parallel branches (22).

According to FIG. 8, the same means (13) consist of a beveled and grooved solid rod (23).

Figure 11:
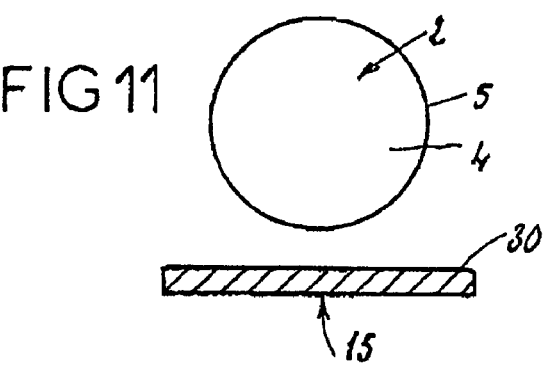

According to FIG. 11, the heat is extracted by radiative exchange and/or convection with a heat sink (30) arranged at a distance from the reaction unit (2), on the same side as its cold end (8). For example, this heat sink (30) consists of a flat PELTIER-effect module.

According to FIGS. 12 and 13, the external medium (6) is a liquid or gaseous fluid phase. To this end, a plate (24) of a plastic material is provided, in which a cavity (24a) for confinement of the reaction volume unit (2) is formed, its reference axis (3) being for example arranged horizontally. This confinement cavity (24a) has a flattened or planar shape, and it is therefore arranged horizontally. This confinement cavity (24a) is furthermore closed by a cover or film (50).

The device represented in FIGS. 12 and 13 may be obtained by any suitable technique, for example microetching in any compatible substrate, such as silicon.

As shown in FIG. 13, the cavity (24a) has any suitable shape, and the internal medium (4) is of a round or oval shape, preferably symmetrical with respect to the reference axis (3), so that the microconvection paths (12) are followed without any physical constraint.

The external medium (6) is confined inside the cavity (24a). It consists of trapped air, for example, creating a round or ovoid interface with said external medium (6) in a section plane parallel to the bottom of the cavity (24a) and the film (50), level with the internal medium (4).

According to FIG. 14, the means (13) for forming and/or maintaining the reaction unit (2) consist of a conical tube (16), at the free end (16a) of which are contained or integrated the heating means (14), obtained by a resistive effect in the case of a metal tube.

According to the same FIG. 14, a mobile reaction component, for example a rod (40), is arranged inside the tube (16) and comprises a reactive surface (9) having a hydrodynamic shape at its free end, for example a trepan shape. This reaction component can be moved between two positions, namely an inactive position outside the reaction unit (2) and an active position in which the reactive surface (9) is immersed in the internal medium (4) forming the reaction unit (2).

After the method has been carried out, the analyte (1) bound to the reactive surface (9) is of course determined by any suitable means, in two different ways, namely:

either the reactive surface remains in contact with the internal medium (4) during the determination, or the reactive surface is arranged away from the internal medium (4) at the time of the determination.

The relevance of the microanalysis principles explained above was demonstrated according to the following experimental protocol:

An internal liquid medium (4) is first provided, consisting of a so-called TeNaCl buffer having the following composition: Triton X100 0.05%, Tris 10 mM Ph8, EDTA, NaCl 1 M, salmon sperm DNA at 0.05%.

So-called DIPF-8831 fluorescent microbeads available from MOLECULAR PROBES are dispersed and suspended in this liquid medium. The concentration of these microbeads is of the order of 500 units per µl.

The density of these microbeads is of the order of 1.05 g/ml, which is close to the density of the internal medium (4).

According to FIG. 1, a metal capillary tube (16) having an internal diameter of 2 mm at its end is provided, the free end (16a) of which is beveled. This free end is lined on the inside with a hydrophilic coating (17) consisting of Bovine Serum Albumin (BSA) The same free end is heated by a resistive effect, as described or shown with reference to FIG. 14.

Using the tube (16) and the internal medium (4) exemplified above, in which the aforementioned microbeads are suspended, a reaction unit (2) having the shape of a drop, the diameter of which lies between 1 and 2.5 mm, is formed at the free end (16a).

Heat is extracted by providing a flat cooling element (30), as shown in FIG. 6, that is to say by radiative exchange and/or convection with the cold end (8) of the unit (2). The temperature difference generating the thermal gradient (66) is preferably regulated to a value of between 10 and 65° C.

As shown by the experimental setup according to FIG. 15, the reaction unit (2) is illuminated using a He-Ne laser beam with a wavelength of 633 nm, while the aforementioned fluorescent microbeads absorb at a wavelength of 625 nm and re-emit at 645 nm. The laser illumination is collimated so as to define an extremely thin plane (27), having a thickness of between 50 and 100 µm, where it passes through the reaction unit (2) This plane is observed using a CDD camera (29), the images acquired in this way being processed by any suitable system (28).

Using this experimental setup, the existence of a forced microconvection according to the above definition could be established, the rate of which varies roughly from 80 to 190 µm/s.

In general, the operational steps described and exemplified above may be generalized to any method for isolating an analyte (1) from an initial liquid sample containing it, on a reactive surface (9) in contact with some or all of the initial sample, consisting in carrying out the following steps:

1) forming and/or maintaining a reaction volume unit (2), comprising an internal liquid medium (4) corresponding to some or all of the initial sample, the unit (2) having an interface (5) with an external medium (6) and having a surface tension with respect to it, 2) applying a temperature difference between at least two thermal points lying:
in the vicinity of and/or
at the surface of and/or
inside the unit (2), said thermal points being respectively different as regards their temperatures and positioning, 3) fixing the analyte (1) on the reactive surface (9) positioned in the path of forced convection generated by the temperature difference.

This method may furthermore be characterized by the following steps (1) to (3):

1) forming and/or maintaining a reaction volume unit (2) having a shape which is symmetrical about a reference axis (3), consisting only of the so-called internal liquid medium (4) in which the analyte (1) obtained from some or all of the initial sample is distributed, said reaction unit having an interface (5) with the optionally confined external medium (6), which is different to the internal medium, and having a surface tension with respect to it, said interface having a closed developed surface about said reference axis (3), 2) generating a thermal gradient (66) through the reaction unit (2) along the reference axis (3), so as to define a hot region (7) and a cold region (8) therein and to induce a variation in the surface tension of the interface (5), parallel to the reference axis (3), and to set the internal medium (4) in motion along a closed path (12) of forced microconvection, comprising an axial forward circulation (12a) from the cold region (8) to the hot region (7) and a peripheral return circulation (12b) from the hot region to the cold region, 3) placing the reactive surface (9) in the forced microconvection path (12) of said internal medium.

The reactive surface (9) may comprise a surface independent of the thermal points which generate the temperature difference (6), or a surface belonging to the region (7) or the region (8).

The invention claimed is:

1. A method for isolating an analyte from an initial sample containing it, on a reactive surface in contact with some or all of the initial sample, comprising the following steps:

1) forming and/or maintaining a reaction volume unit, comprising an internal liquid medium corresponding to some or all of the initial sample, the unit having an interface with an external medium and having a surface tension with respect to it, 2) applying a temperature difference between at least two thermal points lying:
in the vicinity of and/or
at the surface of and/or
inside
the unit, said thermal points being respectively different as regards their temperatures and positioning, said temperature difference creating a path of forced convection within said reaction volume unit 3) placing a reactive surface in said path of forced convection, and fixing the analyte on the reactive surface positioned in the path of forced convection generated by the temperature difference.

2. The method as claimed in claim 1, further comprising the within steps (1) to (3):

1) wherein said forming and/or maintaining the reaction volume unit comprises for the duration of said step forming the reaction volume unit having a shape which is symmetrical about a reference axis, consisting only of the internal liquid medium in which the analyte obtained from some or all of the initial sample is distributed, said reaction volume unit having an interface with the optionally confined external medium, which is different to the internal medium, and having a surface tension with respect to it, said interface having a closed developed surface about said reference axis, 2) wherein said applying a temperature difference comprises generating a thermal gradient through the reaction volume unit along the reference axis, so as to define a hot region and a cold region therein and to induce a variation in the surface tension of the interface, parallel to the reference axis, and to set the internal medium in motion along a closed path of forced microconvection, comprising an axial forward circulation from the cold region to the hot region and a peripheral return circulation from the hot region to the cold region, and 3) wherein said placing the reactive surface in the path of forced convection comprises placing the reactive surface in the forced microconvection path of said internal medium.

3. The method as claimed in claim 2, wherein the reactive surface comprises a surface independent of the thermal points which generate the temperature difference, or a surface belonging to one said region.

4. The method as claimed in claim 1, wherein the reaction volume unit is a drop.

5. The method as claimed in claim 1, wherein the external medium is air laden with water vapor.

6. The method as claimed in claim 2, wherein the reference axis is arranged vertically, and the thermal gradient is arranged from the bottom upward.

7. The method as claimed in claim 6, wherein the thermal gradient is generated by supplying heat to the internal medium in the hot region of the reaction unit; and the heat is supplied by conductive exchange with a heating element arranged at least partly inside the internal medium, on the same side as its hot region.

8. The method as claimed in claim 2, wherein the reactive surface is immersed in the internal medium, between the hot region and the cold region.

9. The method as claimed in claim 7, the analyte being bound to a particle, wherein firstly the particle comprising a support and a capture agent for the analyte, which is bound to said support, the binding between said support and said capture agent and/or between the capture agent and the analyte being labile at the temperature of the hot region of the reaction unit, and effective at any temperature lying between that of the hot region and that of the cold region of said reaction unit, and secondly the particle is distributed and suspended in the internal medium of the reaction unit.

10. The method as claimed in claim 9, wherein the particle is a magnetic particle that can be trapped by a magnetic source, such as a magnet.

11. The method as claimed in claim 2, wherein the magnetic source which can trap the magnetic particles is located level with or belongs to the means generating the hot region.

12. The method as claimed in claim 1, wherein a step of reading and/or detection is carried out in contact with the internal medium away from said internal medium, after the analyte has been fixed to the reactive surface.

13. The method as claimed in claim 1, wherein the temperature of the hot region of the reaction unit is maintained at a value lower than the boiling temperature of the internal medium, and the temperature of the cold region of said unit is maintained at a value higher than the freezing temperature of said internal medium.

14. The method as claimed in claim 2, wherein the rate of the forced microconvection of the internal medium is controlled by variation of the temperature difference between the hot and cold regions.

* * * * *